United States Patent
Chang

[11] Patent Number: 5,339,476
[45] Date of Patent: Aug. 23, 1994

[54] POWERED TOOTHBRUSH

[76] Inventor: Shun-Der Chang, 10th Fl., No. 38-2, Dah-Duen 16th St., Taichung, Taiwan

[21] Appl. No.: 75,736
[22] Filed: Jun. 11, 1993
[51] Int. Cl.⁵ .............................................. A61C 17/30
[52] U.S. Cl. .................................................. 15/28
[58] Field of Search ..................................... 15/28, 29

[56] References Cited
U.S. PATENT DOCUMENTS

| | | | |
|---|---|---|---|
| 3,242,516 | 3/1966 | Cantor | 15/28 |
| 3,802,420 | 4/1974 | Moffat | 15/28 |
| 4,274,173 | 6/1981 | Cohen | 15/28 |
| 5,088,145 | 2/1992 | Whitefield | 15/28 |

Primary Examiner—Edward L. Roberts
Attorney, Agent, or Firm—Weingarten, Schurgin, Gagnebin & Hayes

[57] ABSTRACT

A powered toothbrush with rotary bundles of bristles includes a driver installed in the handle portion of the toothbrush and a plurality of driven rotors in the head portion. A plurality of bundles of bristles are respectively attached to the driven rotors to rotate therewith. A belt is provided between the driver and the driven rotors to transmit rotation from driver to the driven rotors.

10 Claims, 2 Drawing Sheets

POWERED TOOTHBRUSH

BACKGROUND OF THE INVENTION

The present invention relates to a powered toothbrush with rotary bundles of bristles, and, more particularly, to a novel rotation driving mechanism for the rotation of the bristles thereof.

The cleaning effect of powered toothbrushes has been verified. In the markets, there are two types of powered toothbrushes, one type concerns those generating pressured jets of water (for example, the toothbrushes sold under the brand of "Waterpik") and the other type concerns those having rotary bundles of bristles (for example, those sold under the brand of "Interplak"). Conventional powered toothbrushes with rotary bundles of bristles (hereafter this type of powered toothbrushes is referred to simply as "powered toothbrushes") are equipped with pinions and bundles of bristles respectively fixedly attached to the pinions to rotate therewith. A driving gear receives a rotating force from an outside power source to drive the pinions via shaft means or link means. The said conventional powered toothbrushes equipped with rotation driving mechanisms constituted of gears, pinions, and shaft means or link means encumber them with some disadvantages: a heavy weight, a high manufacturing cost, a complex structure, and, an occurrence of a disgusting noise during operation thereof.

SUMMARY OF THE INVENTION

To overcome the disadvantages of the conventional powered toothbrushes, the present invention is proposed to have a unique powered driving mechanism for rotating the bristles. The rotation driving mechanism of the present invention has the advantages of a light weight, a low cost, a simple structure and a quite operation during use thereof.

The present invention comprises an elongate main body which defines a cavity and which has a head portion and a handle portion; a lower bearing plate which has a shape similar to the contour of the cavity of the main body, is received inside the cavity portion; an upper bearing plate which has a configuration similar to that of the lower bearing plate, is mounted over the main body and also functions as a cover for the cavity portion; a driver which is mounted between the lower and upper bearing plates and rotates within the handle portion, receives a rotation force from a power source; a plurality of driven rotors are mounted between the bearing plates and rotate within the head portion; flexible force transmission means connecting the driver and some of the driven rotors to transmit rotation force from the driver to the driven rotors; a plurality of bundles of bristles respectively have ends fixedly attached to the driven rotors to rotate therewith.

It is an object of the present invention to provide a powered toothbrush having a light weight.

It is a further object of the present invention to provide a powered toothbrush having a low cost.

It is still another object of the present invention to provide a powered toothbrush having a simple construction.

It is yet another object of the present invention to provide a powered toothbrush having a quiet operation during use.

Other objects, advantages, and novel features of the invention will become more apparent from the following detailed description when taken in conjunction with the accompanying drawings.

DETAILED DESCRIPTION OF THE PREFERRED EMBODIMENTS

Figure 1:
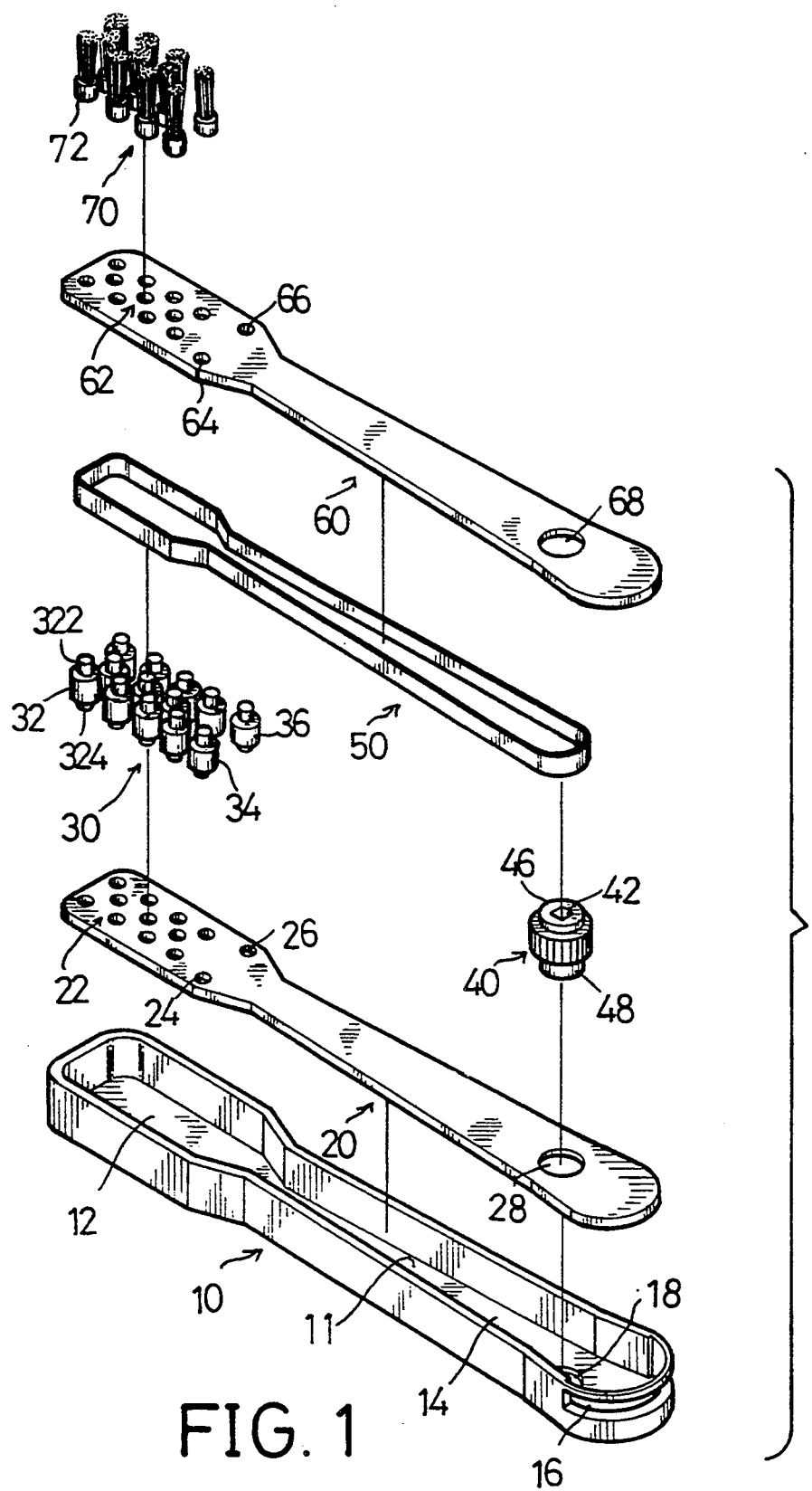
FIG. 1 is a perspective exploded view of an embodiment of the powered toothbrush of the present invention.

Referring to the drawings and initially to FIG. 1, a perspective exploded view, a powered toothbrush in accordance with the present invention generally includes an elongate main body 10 which defines a cavity 11, a lower bearing plate 20, eleven driven rotors 30, two idle rotors 34 and 36, a driver 40, an open belt 50, an upper bearing plate 60, and eleven bundles of bristles 70.

Figure 3:
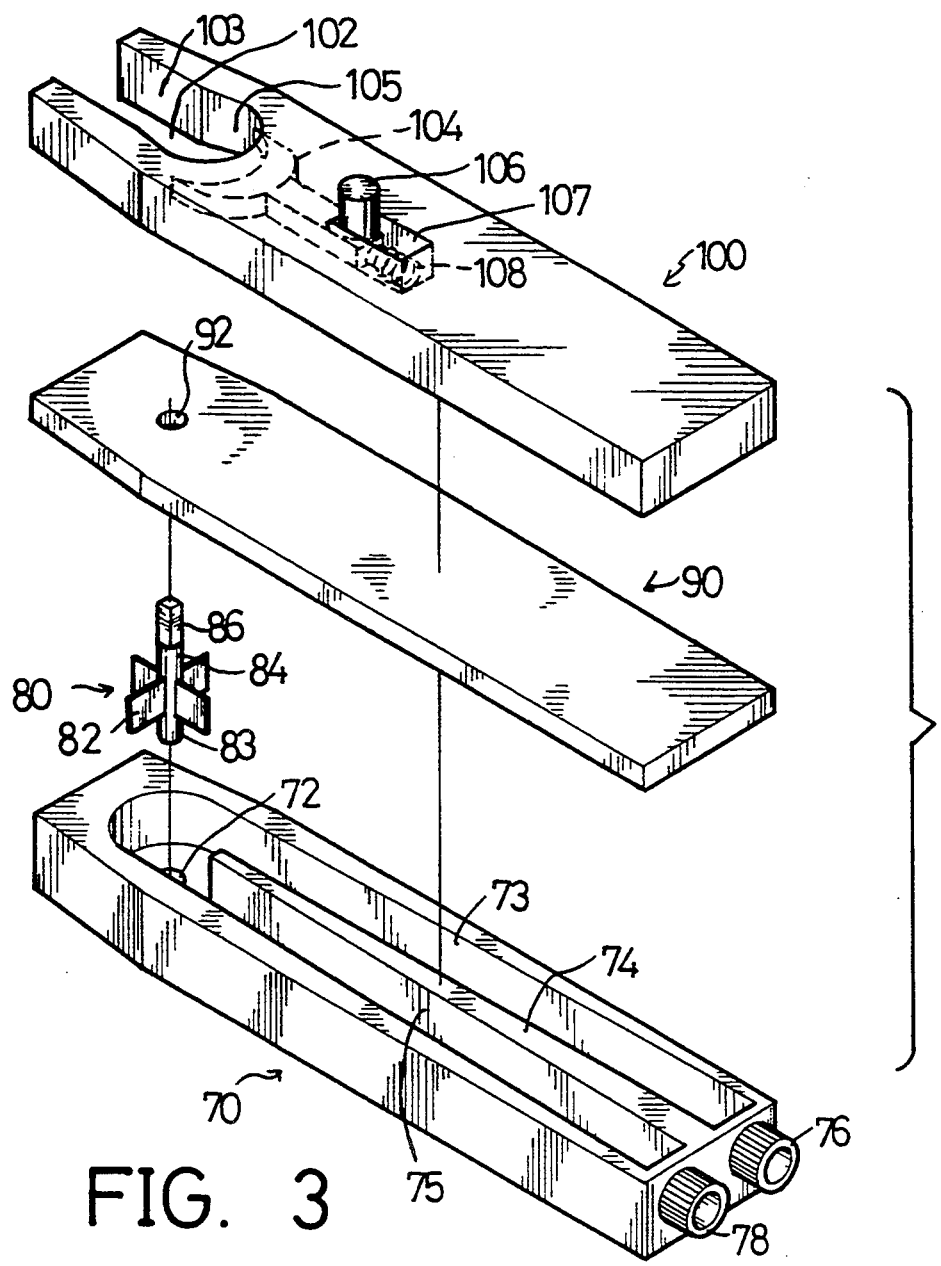
FIG. 3 is an perspective exploded view showing an optional power source apparatus for providing driving power to the powered toothbrush of the present invention.

The main body 10 has a head portion 12 and a handle portion 14. On the handle portion 14, there is a circular bearing recess 18 formed on the bottom wall of the main body 10 and a groove 16 formed on an end wall thereof. The bearing recess 18 is used to receive a lower bearing portion 48 of a driver 40, and, the groove 16 is used to engage with a fork 104 (referring to FIG. 3) when the present invention is mounted on and powered by a power source apparatus as shown by FIG. 3.

When all of the parts of the present invention are assembled together, the lower bearing plate 20 which has a shape similar to the contour of the cavity 11 of the main body 10, is received within the cavity 11 thereof. The lower bearing plate 20 has eleven bearing holes 22 formed about the hand portion thereof. The bearing holes 22 are arranged in three rows which extend substantially along the lengthwise direction of the toothbrush. Each of the outer rows of the bearing holes 22 has four holes, and, the middle row thereof has three holes. The bearing holes 22 are used to receive respectively lower bearing portions of driven rotors 30 (for example, the lower bearing portion 324 of the driven rotor 32). About the hand portion of the lower bearing plate 20, there is a bearing hole 28 which is arranged concentrically to the bearing recess 18 and has a diameter substantially similar thereto. The bearing hole 28, as the bearing recess 18, is also used to receive the lower bearing portion 48 of the driver 40. Positioned longitudinally between the bearing holes 22 and the bearing hole there are two additional bearing holes 24, 26 wherein each hole has a diameter substantially similar to that of the bearing holes 22. The two bearing holes 24 and 26 are used receive respectively two idle rotors 34 and 36. The function of the idle rotors 34, 36 will be explained in the following disclosures.

The eleven driven rotors 30 have lower bearing portions (for example, the lower bearing portion 324 of the driven rotor 32) which are respectively received by the bearing holes 22 of the lower bearing plate 20 and can rotate therein. Furthermore, the rotors 30 have upper bearing portions (for example, the upper portion 322 of the driven rotor 32) which are received respectively in bearing holes 62 of the upper bearing plate 60. It can be better seen from FIG. 2, when the driven rotors 30 are mounted on their respective positions, each driven rotor of the middle row contacts with its neighboring four driven rotors located on the outer rows, but does not contact with other middle row rotors. Furthermore, the driven rotors of the outer rows do not contact with each other.

Turning back to FIG. 1, the two idle rotors 34 and 36 which have configuration similar to that of the driven rotors. 30, are received respectively on the bearing holes 24 and 26.

The driver 40 has a lower bearing portion 48 which is received by the bearing hole 28 and recess 18, an upper bearing portion 46 which is received in a bearing hole 68 of the upper bearing plate 60. On the upper bearing portion 46, the driver 40 has a square recess 42 which has a shape corresponding to that of a square shank 86 of a water wheel 80 (FIG. 3); thus, a rotation of the water wheel 80 can rotate the driver 40 when the square recess 42 is engaged with the square shank 86. This will be described in greater detail at a later stage.

The open belt 50 is used to tightly enclose the driver 40 and the driven rotors 30 and connects the driver 40 with the driven rotors of the outer rows; thus, the open belt 50 can transmit a rotation force from the driver 40 to the driven rotors.

An upper bearing plate 60 which has a configuration similar to that of the lower bearing plate 20, is used to receive the upper bearing portions of the rotors 30, 34, 36 and driver 40 by bearing holes 62, 64, 66 and 68. The upper bearing plate 60 is fixedly attached to the main body 10 by a known manner, for example, by gluing. The upper bearing plate also functions as a cover for the concave portion of the main body 10.

Eleven bundles of bristles 70 have respective end portions (for example, the end portion 72) which are fixedly attached to the upper bearing portions (for example, the upper bearing portion 322) of the driven rotors which are protrudent beyond the upper bearing plate 60. Thus, the bundles of bristles 70 can be rotated with the driven rotors 30. The attachment of the bundles of bristles 70 to the driven rotors 30 can be achieved by a known manner, for example, by gluing.

Figure 2:
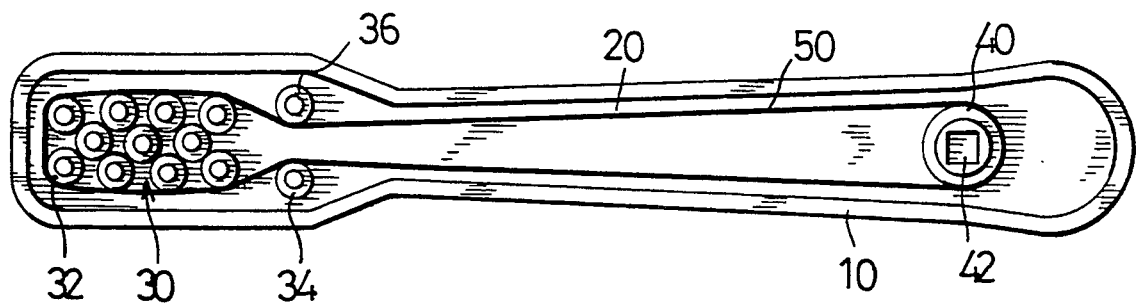
FIG. 2 is a top plan view of the powered toothbrush of FIG. 1 in an assembled state, wherein the cover bearing plate is removed therefrom.

FIG. 2 showing the assembled state of the powered toothbrush of the present invention wherein the upper bearing plate 60 is removed therefrom. From the FIG. 2, it can be clearly understood that when the driver 40 rotates in a direction (for example, clockwise), the open belt 50 can also have a clockwise like rotation. Since each of the driven rotors of the outer rows contacts with the open belt 50, they also have an clockwise rotation. Furthermore, since each of the driven rotors of the middle row only contacts with its corresponding neighboring four outer rotors, each of the rotors in the middle row has a counterclockwise rotation.

The two idle rotors 34 and 36 located between the driver 40 and the driven rotors 30 are arranged so that they laterally compress two sides of the open belt 50 toward each other, whereby the tension of the open belt 50 can be increased to assure that the open belt 50 contacts with every driven rotor located on the outer rows. By the idle rotors 34 and 36, the present powered toothbrush can obtain an effective power transmission.

It can be clearly appreciated that the present invention can use a crossed belt to replace the open belt 50. Under this condition, the two idle rotors 34 and 36 are no longer necessary.

Now, please refer to FIG. 3, an exploded perspective view of an optional power source apparatus for providing rotation force to the present powered toothbrush. The power source apparatus is disclosed in order to help readers to more clearly understand the operation of the present powered toothbrush. However, the power source apparatus does not limit the scope of the present invention. The power source apparatus approximately comprises four parts: a housing 70, a water wheel 80, a cover 90, and a top plate 100 for attaching the powered toothbrush to the power source apparatus.

The top plate 100 is equipped with a rod 106 which is movable along a slot 108 formed on the top plate 100. A tension spring 107 is mounted within the slot 108 by attaching one of its ends to a wall of the slot 108 and the other end to an end of the fork 104. The fork 104 is movable within the top plate 100.

When the four parts are assembled, the lower bearing portion 83 of the water wheel 80 is received by a bearing circular recess 72 formed on the bottom wall of the housing 70. The cover 90 is fixedly attached to the housing by a known manner, and the bearing hole 92 of the cover 90 passes over a square shank 86 and surrounds an upper bearing portion 84 of the water wheel 80. The top plate 100 is fixedly attached to the cover 90 by a known manner.

When a user wants to use the powered toothbrush, he firstly pulls the rod 106 connected with the fork 104 rearwardly (a right down direction of FIG. 3) along the slot 108 to make the front portion of the fork 104 leave the opening 102. Then, the handle portion 14 of the toothbrush is inserted into the opening 102 and the square recess 42 of the rotor 40 is closely engaged with the square shank 86. Thereafter, the pulling force on the rod 106 is released, and the tension of the spring 108 will push the fork 104 to engage with the groove 16 formed in the handle portion 14 of the main body 10. Due to the opening 102 having a front portion 103 narrower than its arcuate base portion 105, and, the handle portion 14 inserted into the opening 102 having a shape corresponding to the contour of the opening 102, the handle portion 14 can be fixedly received within the opening 102 by the pushing force of the spring 108 via the fork 104.

The housing 70 has a water inlet port 76 and a water outlet port 78 on its one end, wherein the inlet port 76 may be connected to water source (for example, a tap) by a hose (not shown). Furthermore, the housing 70 is equipped with a partition 74 which divides an inner space of the housing into two interconnected channels 73 and 75 used respectively for water inner flow and outer flow. When water is flowing through the inlet port 76 and outlet port 78, the water can impinge a force on blades 82 of the water wheel 80 driving the rotation thereof, which results in the rotation of the driver 40 by the engagement between the square shank 86 and square recess 42.

Although the invention has been explained in relation to its preferred embodiment, it is to be understood that other possible modifications and variations can be made without departing from the spirit and scope of the invention as hereinafter claimed.

I claim:

1. A powered toothbrush, comprising:
    an elongate main body (10) defining a cavity (11), said main body having a head portion (12) and a handle portion (14);

two bearing plates (20, 60) spaced with each other, wherein a first one is received within the cavity (11) of the main body, and, a second one is mounted over the cavity (11) and function as a cover therefor;

a driver (40), adapted to be powered by a power source, rotatably mounted in the handle portion (14) between said bearing plates (20, 60);

a plurality of driven rotors (30) arranged in at least three rows substantially along the longitudinal direction of the toothbrush and rotatably mounted in the head portion (12) between said bearing plates (20, 60), wherein the driven rotors in the same row are not in contact with each other;

a flexible rotation transmission means enclosing the driver (40) and said driven rotors (30) and connecting the driver with some of the driven rotors to transmit rotation force from the driver to the driven rotors;

a bristle means (70) having an end (72) secured to each said driven rotors (30) to rotate therewith.

2. A powered toothbrush as claimed in claim 1, wherein the plurality of driven rotors (30) are arranged in three rows substantially along the longitudinal direction of the toothbrush, and, the driven rotors of the outer rows are spaced with each other a predetermined distance, and, the driven rotors of the middle row respectively contact with their surrounding four outer rotors but do not contact with each other.

3. A powered toothbrush as claimed in claim 2, wherein the driving rotor (40) and driven rotors (30) are rotatably fixed between the bearing plates (20, 60) by bearing holes (28, 22; 68, 62) formed respectively on the bearing plates (20, 60).

4. The powered toothbrush of claim 2, wherein the flexible power transmission means is an open endless belt (50), and wherein said toothbrush further comprises belt tensioning means for increasing the tension of the open endless belt (50) so that the belt can contact with each of the driven rotors of the outer rows.

5. A powered toothbrush as claimed in claim 4, wherein the belt tensioning means is two idle rotors (34, 36) rotatably fixed between the bearing plates (20, 60) and positioned between the driver (40) and the driven rotors (30).

6. A powered toothbrush as claimed in claim 2, wherein the flexible power transmission means is a crossed endless belt.

7. A powered toothbrush as claimed in claim 1, wherein the driving rotor (40) and driven rotors (30) are rotatably fixed between the bearing plates (20, 60) by bearing holes (28, 22; 68, 62) formed respectively on the bearing plates (20; 60).

8. A powered toothbrush of claim 1, wherein the flexible power transmission means is an open endless belt (50), and wherein said toothbrush further comprises belt tensioning means for increasing the tension of the open endless belt (50) so that the belt can contact with each of the driven rotors located at the outermost two rows.

9. A powered toothbrush as claimed in claim 8, wherein the belt tensioning means is two idle rotors (34, 36) rotatably fixed between the bearing plates (20, 60) and positioned between the driver (40) and the driven rotors (30).

10. A powered toothbrush as claimed in claim 1, wherein the flexible power transmission means is a crossed endless belt.

* * * * *

UNITED STATES PATENT AND TRADEMARK OFFICE
CERTIFICATE OF CORRECTION

PATENT NO. : 5,339,476
DATED : August 23, 1994
INVENTOR(S) : Shun-Der Chang

It is certified that error appears in the above-indentified patent and that said Letters Patent is hereby corrected as shown below:

Column 1, line 43, "cavity portion;" should read --cavity;--.

Column 1, line 47, "cavity portion;" should read --cavity--.

Column 3, line 11, "rotors. 30," should read --rotors 30,--.

Column 5, line 4, "function" should read --functions--.

Column 6, line 20, "A powered" should read --The powered--.

Signed and Sealed this

Twenty-first Day of March, 1995

Attest:

BRUCE LEHMAN

Attesting Officer     Commissioner of Patents and Trademarks